(12) United States Patent
Yanagi

(10) Patent No.: US 11,534,062 B2
(45) Date of Patent: Dec. 27, 2022

(54) EYE CHART PRESENTATION DEVICE AND OPHTHALMOLOGIC APPARATUS

(71) Applicant: TOPCON CORPORATION, Tokyo (JP)

(72) Inventor: Eiichi Yanagi, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 364 days.

(21) Appl. No.: 16/816,808

(22) Filed: Mar. 12, 2020

(65) Prior Publication Data
US 2020/0288967 A1    Sep. 17, 2020

(30) Foreign Application Priority Data

Mar. 13, 2019  (JP) .............................. JP2019-046433
Nov. 27, 2019  (JP) .............................. JP2019-214134

(51) Int. Cl.
*A61B 3/032*    (2006.01)
*A61B 90/00*    (2016.01)

(52) U.S. Cl.
CPC .............. *A61B 3/032* (2013.01); *A61B 90/36* (2016.02); *A61B 2090/365* (2016.02); *A61B 2090/3618* (2016.02)

(58) Field of Classification Search
CPC . A61B 3/032; A61B 90/36; A61B 2090/3618; A61B 2090/365; A61B 3/08
See application file for complete search history.

(56) References Cited

U.S. PATENT DOCUMENTS

| 4,626,090 A | * | 12/1986 | Charlier | ............... | A61B 3/0083 |
| | | | | | 351/226 |
| 5,690,551 A | * | 11/1997 | Taki | ....................... | G02B 30/35 |
| | | | | | 345/9 |
| 11,045,085 B2 | * | 6/2021 | Nauche | ................ | A61B 3/0008 |
| 11,099,383 B2 | * | 8/2021 | Furusawa | .......... | G02B 27/0101 |
| 2004/0095556 A1 | * | 5/2004 | Mihashi | ................ | A61B 3/112 |
| | | | | | 351/238 |

(Continued)

FOREIGN PATENT DOCUMENTS

| CN | 201058019 | 5/2008 |
| CN | 106264441 | 1/2017 |

(Continued)

OTHER PUBLICATIONS

Office Action dated Jan. 24, 2022, in Chinese Patent Application No. 202010152619.X with partial English-language translation.

*Primary Examiner* — Phong X Nguyen
(74) *Attorney, Agent, or Firm* — Wenderoth, Lind & Ponack, LLP

(57) ABSTRACT

An eye chart presentation device includes a display to display an eye chart image on a screen, a reflection mirror to reflect light flux emitted from the display, and a convex lens system to form a virtual image of the eye chart image from the light flux reflected by the reflection mirror, the focal length of the convex lens system being greater than 800 mm. The screen is positioned within the focal length of the convex lens system, and the display emits the light flux from a lateral direction with respect to sightline of the eye. The reflection mirror includes a first mirror to directly reflect the light flux from the display and a second mirror to reflect the light flux reflected by the first mirror to the convex lens system.

6 Claims, 3 Drawing Sheets

(56) References Cited

U.S. PATENT DOCUMENTS

| | | | | |
|---|---|---|---|---|
| 2009/0303315 | A1* | 12/2009 | Charlesworth | G02B 23/18 |
| | | | | 359/473 |
| 2015/0042958 | A1* | 2/2015 | Li | A61B 3/0041 |
| | | | | 353/7 |
| 2015/0116666 | A1* | 4/2015 | Cho | A61B 3/1015 |
| | | | | 351/239 |
| 2015/0282704 | A1* | 10/2015 | Maddess | A61B 3/032 |
| | | | | 600/558 |
| 2017/0332896 | A1* | 11/2017 | Inoue | A61B 3/032 |
| 2019/0274539 | A1* | 9/2019 | Nauche | A61B 3/0041 |
| 2020/0015672 | A1* | 1/2020 | Nauche | A61B 3/0008 |
| 2020/0275833 | A1* | 9/2020 | Morino | A61B 3/024 |
| 2021/0011286 | A1* | 1/2021 | Morohashi | G03B 21/28 |
| 2021/0173199 | A1* | 6/2021 | Suzuki | A61B 3/0008 |
| 2022/0024316 | A1* | 1/2022 | Suzuki | B60K 37/02 |

FOREIGN PATENT DOCUMENTS

| | | |
|---|---|---|
| CN | 107157437 | 9/2017 |
| JP | 2013-48753 | 3/2013 |
| JP | 5835838 | 12/2015 |

* cited by examiner

EYE CHART PRESENTATION DEVICE AND OPHTHALMOLOGIC APPARATUS

CROSS-REFERENCE TO RELATED APPLICATION

The present application is based on and claims a priority benefit of Japanese patent application No. 2019-046433, filed on Mar. 13, 2019, as well as a priority benefit of Japanese patent application No. 2019-214134, filed on Nov. 27, 2019. The disclosures of these applications are hereby incorporated herein by reference in their entireties.

BACKGROUND

This disclosure relates to an eye chart presentation device and an ophthalmologic apparatus comprising the same.

An eye chart presentation device has been taught by, for example, JP 5835838 B2. The conventional eye chart presentation device taught by JP 5835838 B2 includes a display to show an eye-chart image, a reflection mirror to reflect light flux emitted from the display, a convex lens system to form a virtual image based on the reflected light flux from the reflection mirror, and an optical path bending mirror to bend the optical path of the reflected light flux passed through the convex lens system and to present the virtual image at a predetermined image point. With this, the conventional eye chart presentation device presents an eye-chart image for optometry.

SUMMARY

In the conventional eye chart presentation device, the light flux emitted from the display is reflected vertically upward by the reflection mirror, and the convex lens system is disposed vertically above the reflection mirror. Therefore, it must ensure that the distance in the height direction from the reflection mirror to the convex lens system is long enough to secure the optical path length necessary for the reflection mirror and the convex lens system, resulting in an increase in the height dimension of the apparatus, disadvantageously. Further, in order to provide the eye chart presentation device on, for example, an optometry table, it is preferable to downsize the apparatus not only in the height direction but also in the depth direction.

An object of the present disclosure is, therefore, to provide an eye chart presentation device capable of downsizing the apparatus both in the height direction and the depth direction while securing the optical path length necessary for a reflection mirror and a convex lens system.

To achieve the above object, an embodiment of an eye chart presentation device described in the present disclosure includes a display to display an eye chart image on a screen, a reflection mirror to reflect light flux emitted from the display, a convex lens system to form a virtual image of the eye chart image based on the light flux reflected by the reflection mirror, and an optical path bending mirror to bend an optical path of the reflected light passing through the convex lens system and to present the virtual image of the eye chart image at an image point away from an eye to be examined by a predetermined distance. The focal length of the convex lens system is set greater than 800 mm. The screen is positioned within the focal length of the convex lens system. The display is arranged to emit the light flux from a lateral direction with respect to sightline of the eye. The reflection mirror includes a first mirror to directly reflect the light flux from the display and at least one second mirror to reflect the light flux reflected by the first mirror to the convex lens system.

DETAILED DESCRIPTION

Figure 1:
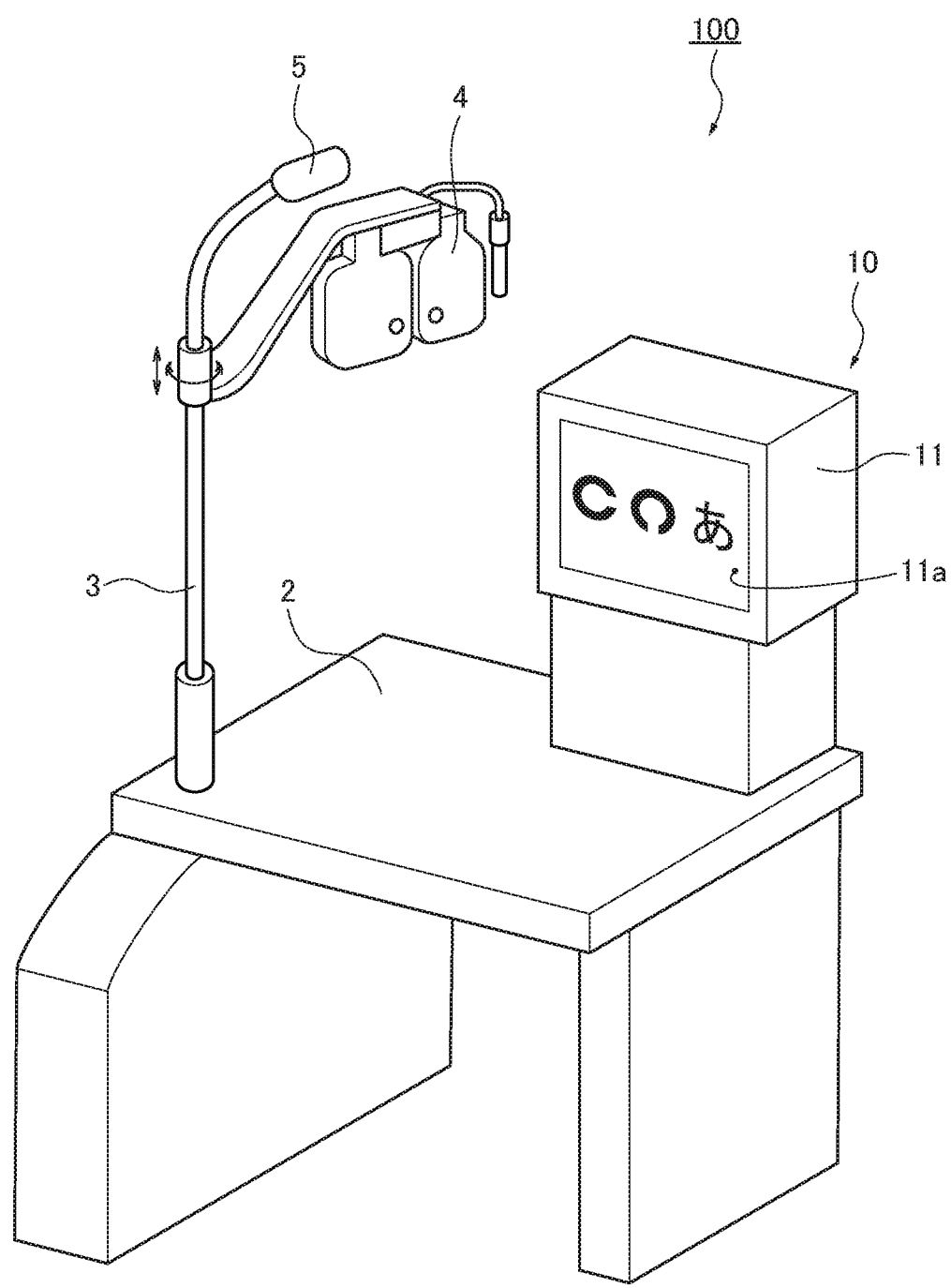
FIG. 1 is a perspective view showing an ophthalmologic apparatus comprising an eye chart presentation device of an embodiment.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

Hereinafter, an embodiment of an eye chart presentation device 10 and an ophthalmologic apparatus 100 comprising the same will be described with reference to the drawings.

The ophthalmologic apparatus 100 is disposed in front of a subject or a patient 1 (shown in FIG. 2) and presents various eye charts to the subject 1. The ophthalmologic apparatus 100 then measures optical characteristics such as refractive power of an eye E to be examined with the cooperation of the subject 1. The ophthalmologic apparatus 100 includes an eye chart presentation device 10, an optometry table 2, an optometry part 4, and a light 5.

As illustrated in FIG. 1, the eye chart presentation device 10 is mounted on the optometry table 2 and is configured to present an eye chart for far-sight examination such as Landolt ring to the subject 1. On the optometry table 2, a supporting post 3 is provided horizontally rotatable, and the optometry part 4 and the light 5 are supported by the supporting post 3. The optometry part 4 includes a plurality of optical elements having different refractive powers. By selectively placing one of the optical elements before the eye E to be examined, the optometry part 4 corrects the visual function of the eye E.

Figure 2:
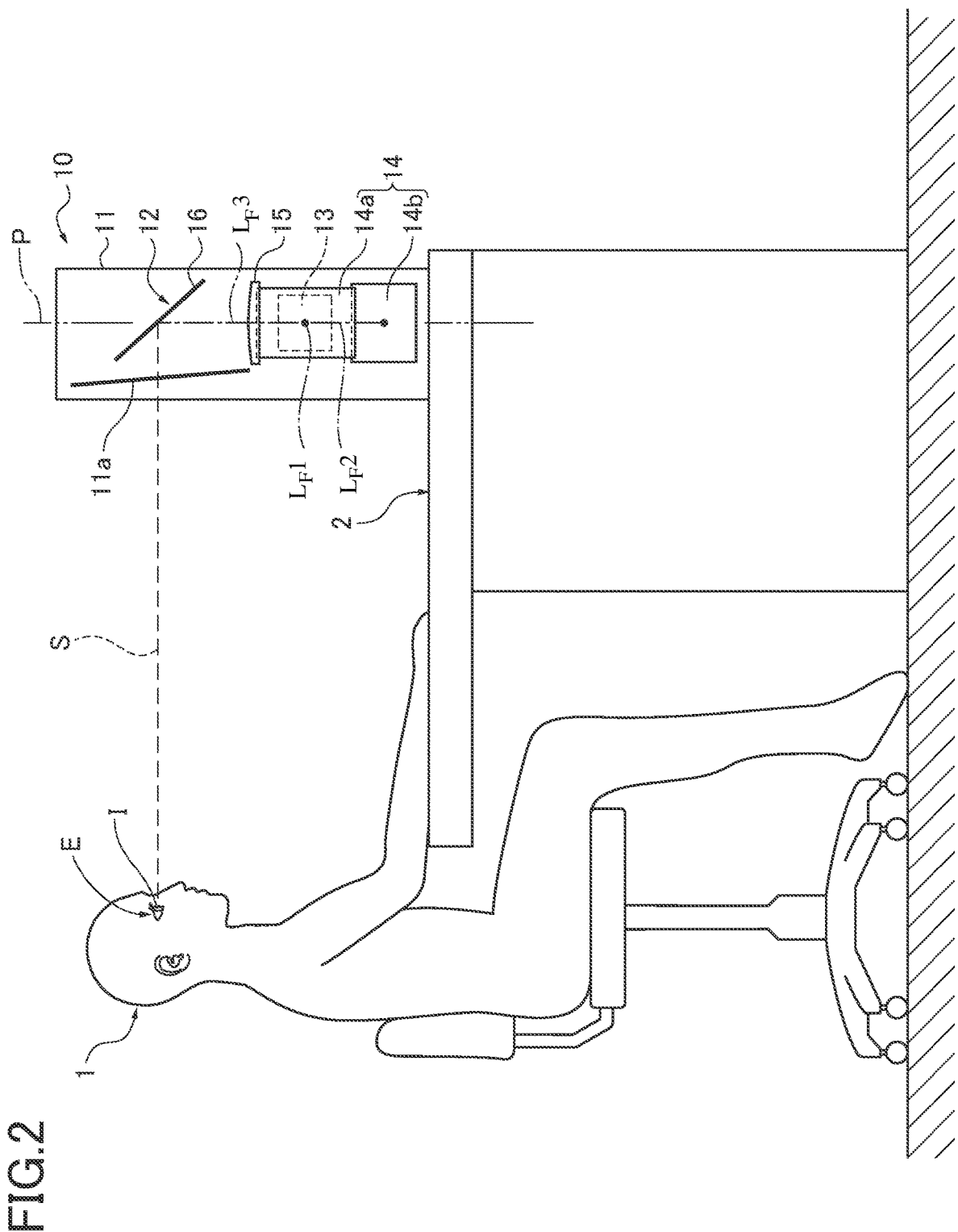
FIG. 2 is a side view illustrating an optical system of the eye chart presentation device of the embodiment.
Figure 3:
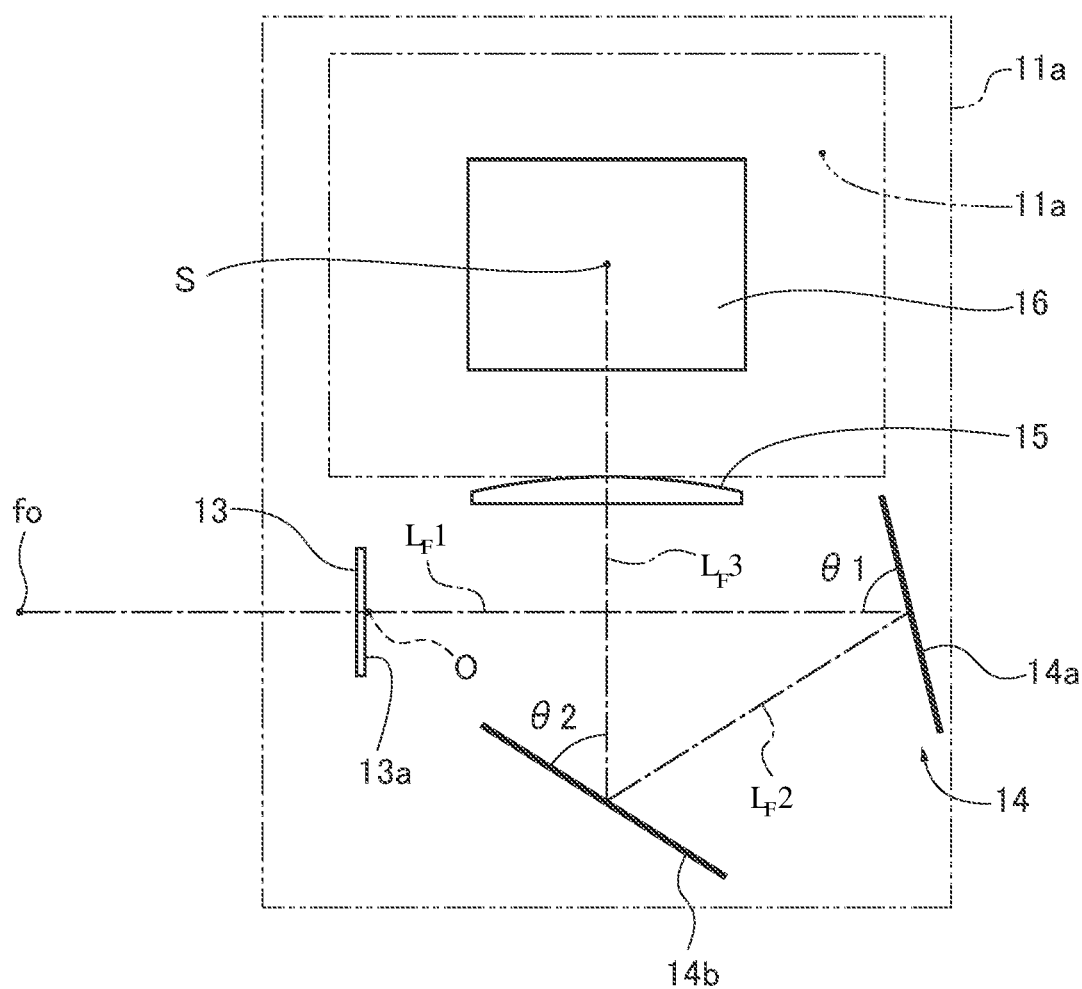
FIG. 3 is a front view illustrating the optical system of the eye chart presentation device of the embodiment.

As illustrated in FIG. 2 and FIG. 3, the eye chart presentation device 10 of the embodiment includes a casing 11 and an optical system 12 for eye chart presentation (hereinafter also simply referred to as "optical system 12") inside the casing 11.

The casing 11 has a substantially cuboid shape and includes support legs (not illustrated) on the bottom surface. The support legs are provided to mount the casing 11 on the optometry table 2. The casing 11 further includes a window 11a on the front surface where the subject faces. The window 11a is a plate member made of a polyacrylate resin and is optically translucent.

The optical system 12 includes a display 13, a reflection mirror 14, a convex lens system 15, and an optical path bending mirror 16.

The display 13 is configured with, for example, a liquid crystal display, and selectively shows eye charts on a screen 13a disposed at an object point O. The display 13 is provided in a lower part of the casing 11 and is arranged at a position so as to emit light flux $L_F1$ in a lateral direction with respect to the direction of a sightline S of the eye E of the subject 1 (i.e., depth direction of eye chart presentation device 10). The light flux $L_F1$ is emitted from the display 13 along a plane P (i.e., out of the paper in a first direction as illustrated in FIG. 2) which intersects with (in embodiment, is orthogonal to) the sightline S of the eye E of the subject 1 (which extends in a second direction). That is, as illustrated in FIG. 3, the display 13 emits the light flux $L_F1$ in the width (first) direction of the eye chart presentation device 10. The emission direction of the light flux $L_F1$ (first direction) is thus orthogonal to the direction of the sightline S (second direction) in the plan view of the eye chart presentation device 10. The screen 13a of the display 13 is arranged to emit the light flux $L_F1$ horizontally.

The reflection mirror 14 reflects the light flux $L_F1$ emitted from the display 13 and guides the reflected light flux to the convex lens system 15. The reflection mirror 14 includes a first mirror 14a and a second mirror 14b. The first mirror 14a directly reflects the light flux $L_F1$, and the second mirror 14b reflects the light flux $L_F2$ reflected by the first mirror 14a in a third direction $L_F3$ and guides the reflected light to the convex lens system 15.

The first mirror 14a is a single mirror which is disposed to horizontally oppose the screen 13a of the display 13, and the reflection surface of the first mirror 14a is oriented below the display 13. In the embodiment, the inclination angle θ1 of the reflection surface of the first mirror 14a is set to 75 degrees with respect to the horizontal direction, and the reflection surface of the first mirror 14a is oriented lower than the horizontal direction. That is, the first mirror 14a reflects the light flux $L_F1$ from the display 13 toward the position below the display 13 along the plane P, which is intersected with (in embodiment, orthogonal to) the sightline S of the eye E of the subject 1.

The second mirror 14b is a single mirror which is disposed at a position lower than the display 13 to reflect the light flux $L_F2$ reflected by the first mirror 14a. To be specific, the second mirror 14b is arranged at a position to vertically oppose the convex lens system 15 and to avoid interference with the light flux $L_F1$ from the display 13. In the embodiment, the second mirror 14b is disposed at a position below the area in which the light flux $L_F1$ from the display 13 passes, and the position of the second mirror 14b is at the midpoint of the display 13 and the first mirror 14a when viewed along the sightline S (i.e., depth direction of device). The reflection surface of the second mirror 14b is oriented upward and is inclined with respect to the vertical direction. The inclination angle θ2 of the reflection surface of the second mirror 14b is set to 60 degree with respect to the vertical direction. That is, the second mirror 14b reflects the light flux $L_F2$ reflected by the first mirror 14a vertically upward along the plane P, which is intersected with (in embodiment, orthogonal to) the sightline S of the eye E of the subject 1. It should be noted that, as shown in FIG. 3, the reflection direction of the reflected light flux $L_F2$ intersects with the emission direction of the light flux $L_F1$ from the display 13 when viewed along the sightline S (i.e., depth direction of device).

The convex lens system 15 transmits the light flux $L_F3$ reflected by the second mirror 14b and forms a virtual image based on the reflected light flux $L_F3$. The convex lens system 15 is disposed at a position higher than the display 13 to avoid interference with the light flux $L_F1$ from the display 13. In the embodiment, the convex lens system 15 is configured with a single plano-convex lens. However, the convex lens system 15 may include two or more lenses. Here, a glass material such as BK7 glass may be used as the plano-convex lens of the convex lens system 15. In this embodiment, the focal distance f of the convex lens system 15 is greater than 800 mm, and is specifically, set to f=1314.0 mm.

In FIG. 3, the reference sign $f_0$ shows the focal point of the convex lens system 15. The object point O is positioned within the focal length f of the convex lens system 15. That is, the display 13 is disposed such that the screen 13a is positioned within the focal length f of the convex lens system 15.

The optical path bending mirror 16 reflects and bends the optical path of the reflected light flux $L_F3$ passed through the convex lens system 15 to present the virtual image at an image point away from the eyepoint I of the eye E of the subject 1 by a predetermined distance. As described above, the focal distance f of the convex lens system 15 is set to f=1314.0 mm. By setting the focal distance f of the convex lens system 15 to be greater than 800 mm, it reduces distortion of the eye-chart image. The inclination angle of the optical path bending mirror 16 is adjustable in accordance with the height of the eye E to be examined from the floor. With this, the optical path bending mirror 16 is able to properly guide the light flux $L_F1$ from the screen 13a to the eye E to be examined. Thus, as shown in FIGS. 2 and 3, the first direction of the light flux $L_F1$ from the screen 13a is orthogonal to the second direction of the sightline S of the eye of the subject 1, and the third direction of the reflected light flux $L_F3$ from the second mirror 14b is essentially orthogonal to both the first direction and the second direction. As a result, it is possible to present the eye chart image to the eye E to be examined appropriately.

Hereinafter, the function and advantageous effects of the ophthalmologic apparatus 100 and the eye chart presentation device 10 of this embodiment will be described.

The ophthalmologic apparatus 100 of the embodiment presents an eye chart image to the subject 1 with the eye chart presentation device 100 in order to measure optical characteristics (e.g., refractive power) of the eye E of the subject 1. To be specific, the operator of the ophthalmologic apparatus 10 manipulates a power switch and a remote controller (not illustrated) of the apparatus 10 to show an eye chart image on the screen 13a of the display 13. The display 13 then horizontally emits the light flux $L_F1$ along the plane P orthogonal to the sightline S of the eye E of the subject 1. That is, the emission direction of the light flux $L_F1$ from the display 13 is orthogonal to the direction of the sightline S (i.e., depth direction of apparatus) in the plan view of the eye chart presentation device 10.

In the eye chart presentation device 10, the screen 13a of the display 13 is opposed to the first mirror 14a of the reflection mirror 14, and the reflection surface of the first mirror 14a faces downward. Therefore, the light flux $L_F1$ emitted horizontally from the display 13 is reflected by the first mirror 14a to a position lower than the display 13 along the plane P.

The second mirror 14b is positioned below the display 13 and reflects the light flux $L_F2$ reflected by the first mirror 14a. As described above, the reflection surface of the second mirror 14b is faced upward and is inclined with respect to the vertical direction. Therefore, the light flux $L_F2$ reflected by the first mirror 14a is reflected vertically upward by the second mirror 14b along the plane P.

The light flux $L_F3$ reflected by the second mirror 14b forms a virtual image as passing through the convex lens system 15. The reflected light flux $L_F3$ passed through the convex lens system 15 is then reflected and bent by the optical path bending mirror 16 to present the virtual image at a predetermined image point.

With the eye chart presentation device 10 of the embodiment, the light flux $L_F1$ is horizontally emitted from the screen 13a of the display 13 and reflected by the first mirror 14a to advance downwardly. The light flux $L_F2$ is then further reflected by the second mirror 14b to advance vertically upward. That is, the light flux $L_F1$ emitted from the display 13 is reflected twice prior to passing through the convex lens system 15. Here, the first mirror 14a reflects and guides the light flux $L_F1$ to a position between the display 13 and the first mirror 14a. That is, the light flux $L_F2$ reflected by the first mirror 14a returns toward the display 13. Additionally, the second mirror 14b is positioned between the display 13 and the first mirror 14a, and the light flux $L_F3$ reflected by the second mirror 14b advances between the display 13 and the first mirror 14a. As a result, the light flux $L_F1$ to $L_F3$ advances within an area between the display 13 and the first mirror 14a. When compared with a convex lens system in which light flux horizontally emitted from a screen is reflected by a reflection mirror only once to bend the optical path once to guide the light flux vertically upward, the eye chart presentation device 10 of the present disclosure is able to reduce the optical length in the height direction without shortening the entire optical length between the screen 13a and the convex lens system 15.

Consequently, it is possible to downsize the eye chart presentation device 10 in the height direction while securing the enough length for the optical length between the screen 13a and the convex lens system 15. When compared with a conventional eye chart presentation device, which has a similar depth dimension to the present disclosure, including a convex lens system in which light flux from the display is straightly reflected to the convex lens system by a single reflection mirror, the eye chart presentation device 10 of the present disclosure is able to reduce the height dimension by about half if the convex lens systems have a focal length of, for example, 800 mm or longer. By reducing the height dimension by about half, it is possible to reduce the volume of the casing by about half.

In the eye chart presentation device 10 of the embodiment, the display 13 horizontally emits the light flux $L_F1$ along the plane H orthogonal to the sightline S of the eye E, and the light flux $L_F1$ is reflected by the first mirror 14a and the second mirror 14b along the plane P. That is, the light flux $L_F1$ as well as the reflected light flux $L_F2$, $L_F3$ are constrained to the plane P. Since the plane P intersects with the sightline S of the eye E which is oriented toward the depth direction of the eye chart presentation device 10, the light flux $L_F1$, $L_F2$, $L_F3$ does not advance in the depth direction of the eye chart presentation device 10. Therefore, it is possible to prevent the eye chart presentation device 10 from being larger in the depth direction and to downsize the eye chart presentation device 10 in the depth direction.

In the embodiment, the light flux $L_F3$ reflected by the second mirror 14b intersects with the light flux $L_F1$ emitted from the display 13 when viewed along the sightline S. The optical path of the reflected light flux $L_F3$ is therefore positioned between the display 13 and the first mirror 14a, thereby the reflection area of the eye chart image can be narrowed. As a result, it is possible to further downsize the eye chart presentation device 10.

In the embodiment, the plane P is arranged to be orthogonal to the sightline S of the eye E of the subject 1. The emission direction of the light flux $L_F1$ from the display 13 is therefore orthogonal to the sightline S in the plan view (i.e., when viewed from above the device 10). Accordingly, it is possible to arrange the display 13, the first mirror 14a and the second mirror 14b at the same position in the depth direction of the device 10, thereby suppressing the size of the eye chart presentation display 10 in the depth direction.

In the embodiment, the first mirror 14a is positioned to be opposed to the screen 13a of the display 13 and reflects the light flux $L_F1$ from the display 13 downwardly. The second mirror 14b is disposed at a position lower than the display 13 to avoid interference with the light flux $L_F1$ from the display 13. The second mirror 14b reflects the light flux $L_F2$ reflected by the first mirror 14a upward. The convex lens system 15 is disposed at a position higher than the display 13 to avoid interference with the light flux $L_F1$ from the display 13.

Accordingly, it is possible to form the second mirror 14b with a single mirror while appropriately guiding the light flux $L_F1$ emitted from the display 13 to the convex lens system 15. That is, it is possible to suppress the increase in the number of the mirrors.

In the embodiment, the screen 13a of the display 13 is oriented to horizontally emit the light flux $L_F1$ therefrom, and the reflection surface of the first mirror 14a is oriented lower than the horizontal direction. With this configuration, it is possible to prevent the dust, etc., to fall on the screen 13a of the display 13 and on the reflection surface of the first mirror 14a. The reflection surface of the second mirror 14b is faced vertically upward, and thus it may be possible to have dust, etc., on the reflection surface of the second mirror 14b. However, since the optical path length from the screen 13a to the second mirror 14b is greater than the optical length from the screen 13a to the first mirror 14a, it is difficult to focus on the reflection surface of the second mirror 14b. That is, even if the reflection surface of the second mirror 14b has some dust, etc., thereon, the subject 1 hardly recognizes the dust, etc. Therefore, the dust, etc., on the second mirror 14b hardly affects the optometry performance.

In the embodiment, the ophthalmologic apparatus 100 is equipped with the above-described eye chart presentation device 10 and the optometry part 4. As it is possible to downsize the eye chart presentation device 10 in the height direction and the depth direction, the eye chart presentation device 10 can be placed on the optometry table 2 of the ophthalmologic apparatus 100, as illustrated in FIG. 1. Therefore, this disclosure achieves space saving of the ophthalmologic apparatus 100.

Although the eye chart presentation device and the ophthalmologic apparatus of the present disclosure have been described in terms of exemplary embodiment, they should not be limited thereto. It should be appreciated that variations or modifications may be made in the embodiment described by persons skilled in the art without departing from the scope of the present invention as defined by the following claims.

For example, in the embodiment, the second mirror 14b in the eye chart presentation device 10 is formed of a single mirror. However, the number of the mirrors forming the second mirror 14b can be two or more as long as the second mirror 14b allows the light flux $L_F2$ reflected by the first mirror 14a to be guided to the convex lens system 15 along an arbitrary plane P.

In the embodiment, the plane P, in which the light flux $L_F1$ from the display 13, the light flux $L_F2$ reflected by the first mirror 14a, and the light flux $L_F3$ reflected by the second mirror 14b advance, is arranged to be orthogonal to the sightline S of the eye E of the subject 1. However, it is possible to reduce the depth dimension of the device 10 if the light flux $L_F1$, $L_F2$, $L_F3$ is guided along a plane that intersects with the sightline S. Therefore, the plane P may be intersected with the sightline S at an angle other than a right angle.

Additionally, the casing 11 of the eye chart presentation device 10 of the embodiment may have short fibers attached to the inner walls of the casing 11 by electrostatic flocking in order to prevent the reflection by the inner wall thereof.

The eye chart presentation device 10 of the embodiment may further include an aperture stop at a position which does not interfere with the light flux $L_F1$ from the display 13. This allows to prevent diffusion light diffused inside the casing 11 from entering the eye E of the subject 1.

In the embodiment, the screen 13*a* of the display 13 is arranged such that the light flux $L_F1$ is emitted horizontally. However, the screen 13*a* may be faced downwardly. This allows to further prevent the dust, etc., to fall on the screen 13*a*.

What is claimed is:

1. An eye chart presentation device comprising:
   a display that is configured to display an eye chart image on a screen;
   a reflection mirror that is configured to reflect light flux emitted from the display;
   a convex lens system that is configured to form a virtual image of the eye chart image based on the light flux reflected by the reflection mirror, the focal length of the convex lens system being greater than 800 mm; and
   an optical path bending mirror that is configured to bend an optical path of the reflected light passing through the convex lens system and to present the virtual image of the eye chart image at an image point away from an eye to be examined by a predetermined distance,
   wherein the screen is positioned within the focal length of the convex lens system,
   wherein the display is arranged to emit the light flux in a first direction,
   wherein a sightline of the eye extends in a second direction orthogonal to the first direction,
   wherein the reflection mirror comprises a first mirror configured to directly reflect the light flux from the display and a second mirror configured to reflect the light flux reflected by the first mirror to the convex lens system in a third direction orthogonal to both the first direction and the second direction,
   wherein the eye chart presentation device is mounted on an optometry table, and
   wherein the display, the reflection mirror, and the convex lens system are arranged so that the optical path of the light flux reflected by the second mirror in the third direction is positioned between the display and the first mirror.

2. The eye chart presentation device according to claim 1, wherein the light flux reflected by the second mirror intersects with the light flux from the display when viewed along the sightline.

3. The eye chart presentation device according to claim 2, wherein the light flux from the display is orthogonal to the sightline in a plan view.

4. The eye chart presentation device according to claim 1, wherein
   the first mirror is positioned to face the screen and reflects the light flux from the display to a position lower than the display,
   the second mirror is positioned lower than the display to avoid interference with the light flux from the display and reflects the light flux reflected by the first mirror upwardly, and
   the convex lens system is positioned higher than the display to avoid interference with the light flux from the display.

5. The eye chart presentation device according to claim 4, wherein
   the display emits the light flux horizontally or downwardly, and
   a reflection surface of the first mirror is oriented lower than the horizontal direction.

6. An ophthalmologic apparatus comprising the eye chart presentation device according to claim 1 and an optometry part configured to correct the visual function of the eye to be examined.

* * * * *